United States Patent

Ramamoorthy et al.

[11] Patent Number: 5,869,755
[45] Date of Patent: Feb. 9, 1999

[54] POROSITY ESTIMATION METHOD IN CARBONATE ROCK

[75] Inventors: Raghu Ramamoorthy, Brighton, Australia; David L. Johnson, Bethel; William F. Murphy, III, Redding, both of Conn.

[73] Assignee: Schlumberger Technology Corporation, Ridgefield, Conn.

[21] Appl. No.: 1,904

[22] Filed: Dec. 31, 1997

[51] Int. Cl.[6] .............................. E21B 49/00; E21B 47/00; G01N 15/08
[52] U.S. Cl. ...................... 73/152.05; 73/38; 166/252.5
[58] Field of Search .................................. 73/152.05, 38, 73/152.02, 152.04, 152.41; 166/252.5, 250.02, 308

[56] References Cited

U.S. PATENT DOCUMENTS

| | | |
|---|---|---|
| 3,483,376 | 12/1969 | Locke et al. . |
| 3,864,569 | 2/1975 | Tittman . |
| 5,036,945 | 8/1991 | Hoyle et al. . |
| 5,055,787 | 10/1991 | Kleinberg et al. . |

OTHER PUBLICATIONS

Anselmetti, F.S. and Eberli, G.P., "Controls on Sonic Velocity in Carbonates," 1993 Pageoph, vol. 141, pp. 287–323.

Brie, A., Johnson, D.L. and Nurmi, R.D., "Effect of Spherical Pores on Sonic and Resistivity Measurements", Proceedings of the SPWLA Twenty–Sixth Annual Logging Symposium, Houston, Texas, Jun. 17–20, 1985, Paper W.

Murphy, W., Reischer, A. and Hsu, K., "Modulus Decomposition of Compressional and Shear Velocities in Sand Bodies," Geophysics, 1985, vol. 58 (2), pp. 227–239.

Berryman, J.G., "Long–Wavelength Propagation in Composite Elastic Media Spherical Inclusions, The Journal of the Acoustical Society of America," 1980, vol. 68, pp. 1809–1831.

*Primary Examiner*—Hezron Williams
*Assistant Examiner*—Jay L. Politzer
*Attorney, Agent, or Firm*—Mark Levy; Keith G. W. Smith

[57] ABSTRACT

An acoustical method of determining the spherical, or vuggy, porosity in carbonate rock formations, as a function of shear modulus. Total porosity and shear modulus of the formation is measured. Then the intrinsic granular porosity, dry bulk modulus, and spherical porosity are calculated. The carbonate rock is modeled, consisting of a primary host medium composed of carbonate grains with intergranular porosity between them. The model is easily modified to account for the case of intercrystalline microporosity existing within the grains, in addition to the intergranular porosity between them.

10 Claims, 1 Drawing Sheet

POROSITY ESTIMATION METHOD IN CARBONATE ROCK

FIELD OF THE INVENTION

The invention pertains to a new method of delineating the different kinds of porosity in carbonate rocks and, more particularly, to a method of using a shear modulus to determine spherical porosity in carbonate rock formations.

BACKGROUND OF THE INVENTION

Interpreting carbonate rock data in well logging is a complex task. Spherical pores in these carbonate formations influence certain parameters (e.g., acoustic moduli, resistivity, and permeability) differently than do typical intergranular porosity. The quantification of spherical porosity (e.g., vuggy, oomoldic, etc.) is essential in order to interpret the facies type of the carbonate rock[1].

A technique developed by Brie et al[2] has been used to determine the extent of spherical porosity in carbonates. The present invention seeks to interpret carbonate hydrocarbon formations using a generalization of the Brie et al method. The current invention comprises a method wherein the shear modulus can be used to isolate the amount of spherical porosity in this type of rock, without the requirement of first obtaining prior knowledge of the pore fluid properties.

It is known that compressional slowness of the carbonate rock can be measured in order to qualitatively estimate spherical porosity. However, currently no quantitative estimate can be made in carbonate rock in the presence of a mixture of unknown pore fluids, such as water, gas, oil, etc.

This invention uses the shear modulus to estimate spherical porosity without the need to know the pore fluid composition. The shear modulus is computed from: a) the shear speed measured by an appropriate sonic logging device, such as a Dipole Shear Sonic Imager (DSI); and b) the formation bulk density as measured, for example, by a Litho-Density Tool (LDT).

The invention relies on a mathematical analysis of the shear acoustic response of carbonate rock formations with a mixture of spherical porosity and conventional intergranular porosity. It provides both a forward model for the theoretical response of the rock having a known mixture of the two pore types, and an inverse model that uses the measured response of the rock to evaluate the constituent volumes of each pore type in the total porosity. It is assumed that the total porosity of the formation is known from a combination of nuclear logs such as a Compensated Neutron Log (CNL) and a Litho-Density Log (LDL) and/or the Nuclear Magnetic Resonance (NMR) log. The Dipole Shear Sonic Imager (DSI), Compensated Neutron Log (CNL), Litho-Density Log (LDL), and the Nuclear Magnetic Resonance (NMR) Log are all commercial well logging services provided by Schlumberger Technology Corporation, the assignee of the present invention. These services and the corresponding tools are described, for example, in U.S. Pat. Nos. 5,036,945 to Hoyle et al (DSI), 3,483,376 to Locke et al. (CNL), 3,864,569 to Tittman (LDL), and 5,055,787 to Kleinberg et al. (NMR/CMR).

SUMMARY OF THE INVENTION

In accordance with the present invention, there is provided a method of estimating the spherical porosity of carbonate rock. First, the total porosity and shear modulus of the formation is measured. Next, the acoustic behavior of the formation, with spherical inclusions, is modeled. The acoustic behavior is modeled through empirical relationships established for the shear and bulk modulus as a function of non-spherical porosity. The model relates the intrinsic intergranular porosity of the medium, the total porosity, and the spherical porosity. Once the total porosity and bulk and shear modulus are known for the pure carbonate medium, spherical and intergranular porosity and the bulk modulus of the rock can be computed. Plotting the spherical porosity derived by this acoustic approach with the spherical porosity derived from petrographic image analysis, shows a good correlation therebetween.

It is an object of the invention to provide an improved method of estimating the spherical porosity of carbonate rock.

It is another object of this invention to provide a technique of estimating the spherical porosity of carbonate rock as a function of the shear modulus.

BRIEF DESCRIPTION OF THE DRAWINGS

A complete understanding of the present invention may be obtained by reference to the accompanying drawings, when considered in conjunction with the subsequent detailed description, in which.

DESCRIPTION OF THE PREFERRED EMBODIMENT

Figure 1:
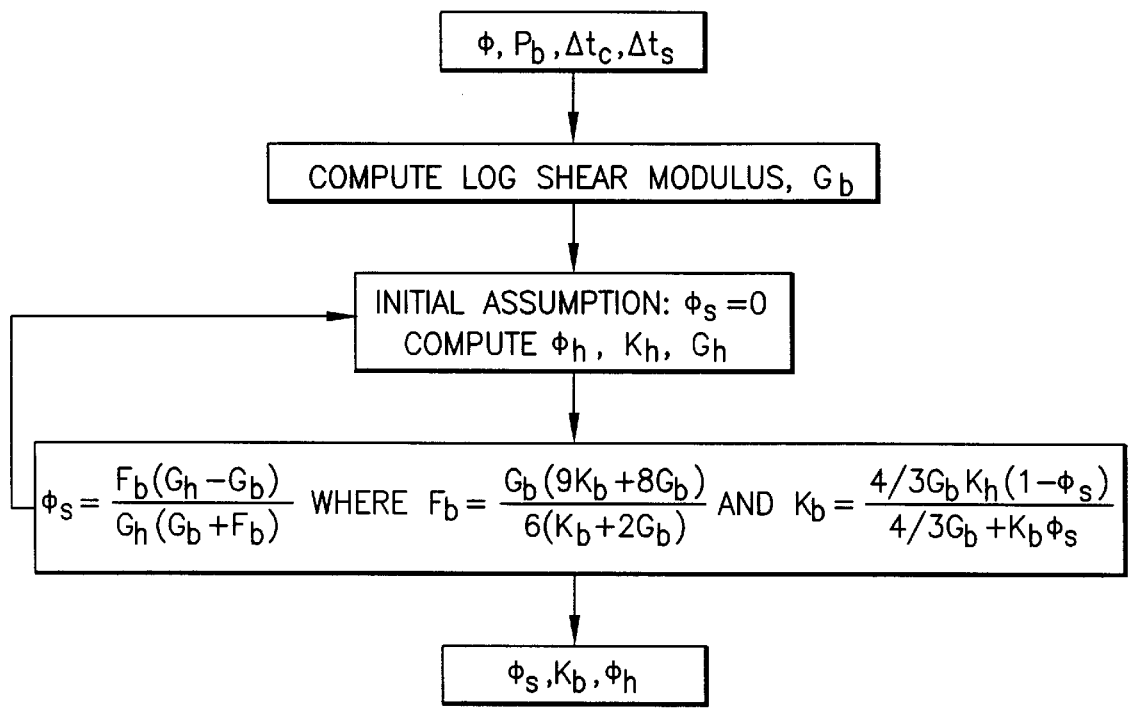
FIG. 1 depicts a flow chart of the acoustic technique of this invention for estimating spherical porosity in carbonate rock.

Generally speaking, the invention uses an acoustical method of determining the spherical, or vuggy, porosity in carbonate rock formations as a function of shear modulus. Total porosity and shear modulus of the formation is measured. Then the intrinsic intergranular porosity, dry bulk modulus, and spherical porosity are calculated. The carbonate rock is modeled, consisting of a primary host medium composed of carbonate grains with intergranular porosity between them. The model is easily modified to account for the case of intercrystalline microporosity existing within the grains, in addition to the intergranular porosity between them. In such a host, the vugs or oomolds can be considered spherical void inclusions.

The acoustic behavior of the intergranular host is modeled through empirical relations that have been established for the shear and bulk modulus as a function of porosity based on the relations originally developed for sandstones by Murphy et al[3]. The relations are expressed as:

$$G_h = G_s \left(1 - \frac{\phi_h}{0.39}\right)\left(1 - \frac{\phi_h}{1.27}\right) \quad (1)$$

$$K_h = K_s \left(1 - \frac{\phi_h}{0.39}\right)\left(1 - \frac{\phi_h}{0.56}\right) \quad (2)$$

where $G_h$ and $K_h$ are the shear and dry bulk moduli, respectively, of the host medium; $G_s$ and $K_s$, are the shear and bulk moduli, respectively, of the pure carbonate mineral at zero porosity and are the moduli for the solid grains; and $\phi_h$ is the intrinsic porosity of the host medium. In the event that the grains themselves possess intercrystalline microporosity (intragranular porosity), equations (1) and (2) are modified as:

$$G_h = G_s \left(1 - \frac{\phi_\mu}{0.39}\right)\left(1 - \frac{\phi_\mu}{1.27}\right)\left(1 - \frac{\phi_m}{0.39}\right)\left(1 - \frac{\phi_m}{1.27}\right) \quad (3)$$

$$K_h = K_s \left(1 - \frac{\phi_\mu}{0.39}\right)\left(1 - \frac{\phi_\mu}{0.56}\right)\left(1 - \frac{\phi_m}{0.39}\right)\left(1 - \frac{\phi_m}{0.56}\right) \quad (4)$$

Here $\phi_\mu$ is the intrinsic microporosity of the grains, while $\phi_m$ is the macro intergranular porosity. In order to correct for the effect of microporosity, it is necessary that a measure of the microporosity be independently obtained from another source, such as the Combinable Magnetic Resonance (CMR) log. However, since the effect of microporosity is minimal, it can be ignored. In most cases, equations (1) and (2) can be used directly.

The model relates the intrinsic intergranular porosity of the host medium, $\phi_h$, the total porosity, $\phi$, and the spherical porosity, $\phi_s$, as follows:

$$\phi_h = (\phi - \phi_s)/(1 - \phi_s) \quad (5)$$

The acoustic response of the rock with spherical inclusions in the intergranular host is modeled using the self consistent scattering approach of Berryman[4]. Knowing the total porosity, spherical porosity and bulk and shear modulus of the pure mineral, the bulk and shear modulus of the dry rock ($K_b$, $G_b$) can be computed from the implicit equations given below:

$$K_b = \frac{\frac{4}{3} G_b K_h (1 - \phi_s)}{\frac{4}{3} G_b + \phi_s K_h} \quad (6)$$

$$G_b = \frac{F_b G_h (1 - \phi_s)}{F_b + \phi_s G_h} \quad (7)$$

where $$F_b = \frac{G_b(9K_b + 8G_b)}{6(K_b + 2G_b)} \quad (8)$$

$G_h$ and $K_h$ are obtained from equations (1) and (2). The solution is iterative, and converges rapidly, since equations (6), (7) and (8) are implicit.

Using the dry bulk modulus, the wet bulk modulus measurements derived from P-wave velocity logs are used to deduce the pore fluid compressibility via the Biot-Gassmann equation as described in "Modulus Decomposition of Compressional and Shear Velocities in Sand Bodies".[3]

Interpretation of Well Data

Referring to FIG. 1, a flow chart of the acoustic processing method of this invention is illustrated. In interpreting well log data, first begin with a measure of the total porosity and shear modulus of the formation. Then invert the above scheme to compute the spherical porosity, dry bulk modulus and intrinsic intergranular porosity. The flowchart graphically demonstrates the interpretation scheme.

Figure 2:
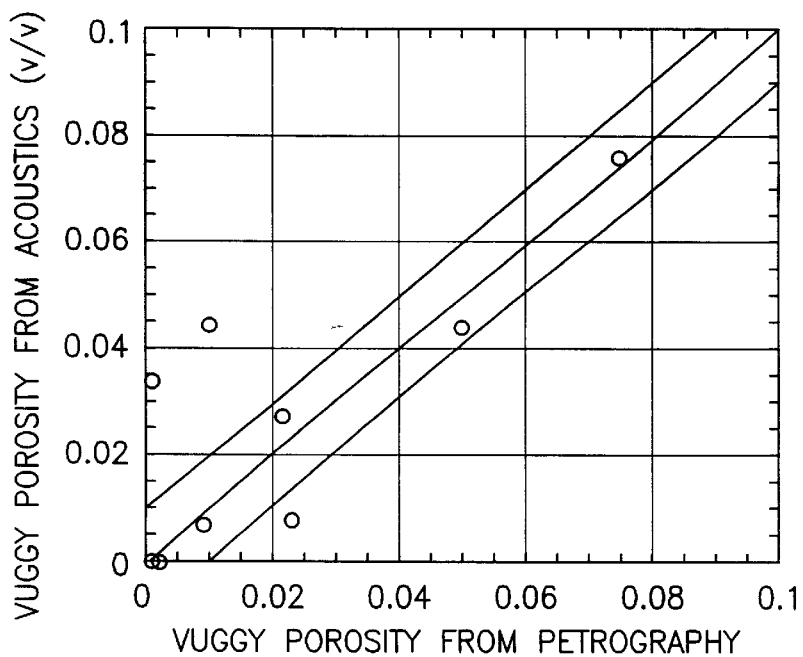
FIG. 2 illustrates a graphical diagram of the comparison between the acoustic spherical porosity determined by this invention versus that derived by petrography.

Referring to FIG. 2, a graph is shown of the spherical (vuggy) porosity obtained from acoustics versus the spherical porosity obtained from petrographic image analysis. In the sample of rock chosen, petrography indicated that the vugs were nearly spherical. This was closely correlated with the mathematical assumption. It can be observed that there is a good correspondence between values obtained by the two different methods. The inventive method is an accurate means of determining spherical porosity. Spherical porosity from vugs and oomolds is crucial to the evaluation of carbonate formations, and the invention provides a means by which this information can be accurately obtained.

REFERENCES

1. Anselmetti, F. S and Eberli, G. P., "Controls on Sonic Velocity in Carbonates," 1993 Pageoph, Vol 141, pp. 287–323.

2. Brie, A., Johnson, D.L. and Nurmi, R.D., "Effect of Spherical Pores on Sonic and Resistivity Measurements", Proceedings of the SPWLA Twenty-Sixth Annual Logging Symposium, Houston, Texas, Jun. 17–20, 1985, Paper W.

3. Murphy, W., Reischer, A. and Hsu, K., "Modulus Decomposition of Compressional and Shear Velocities in Sand Bodies," Geophysics, 1985, Vol. 58 (2), pp. 227–239.

4. Berryman, J. G., "Long-Wavelength Propagation in Composite Elastic Media Spherical Inclusions, " The Journal of the Acoustical Society of America, 1980, Vol. 68, pp. 1809–1831.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method of quantitatively determining spherical porosity in carbonate rock using a shear modulus, and without knowing pore fluid properties, said method comprising the steps of:
   a) obtaining a shear modulus for said carbonate rock;
   b) obtaining total porosity for said carbonate rock;
   c) computing shear modulus of dry carbonate rock; and
   d) using said shear moduli obtained in step (c) to determine said spherical porosity of said carbonate rock.

2. The method in accordance with claim 1, wherein said bulk and shear moduli of step (c) are iteratively computed.

3. The method in accordance with claim 1, further comprising the step of:
   e) relating intrinsic intergranular and intragranular porosity, total porosity, and spherical porosity in order to provide an acoustic response model for said carbonate rock, in conjunction with step (c).

4. The method in accordance with claim 1, further comprising the step of:
   e) computing dry bulk modulus of the carbonate rock formation.

5. The method in accordance with claim 4, further comprising the step of:
   f) using said dry bulk modulus to determine pore fluid compressibility.

6. The method in accordance with claim 1, further comprising the step of:
   e) computing intrinsic intergranular and intragranular porosity of the carbonate rock formation.

7. A method of estimating the spherical porosity of carbonate rock, comprising the steps of:
   a) measuring total porosity and shear modulus of a carbonate rock formation;
   b) modeling acoustic behavior of the carbonate rock formation with spherical inclusions using empirical relationships established for the shear moduli as a function of non-spherical porosity; and c) using the model generated in step (b) to relate the intrinsic intergranular and intragranular porosity of the medium, the total porosity, and the spherical porosity, in order to compute the spherical porosity for the carbonate rock formation.

8. The method in accordance with claim 7, further comprising the step of:

d) using the model generated in step (b) to compute dry bulk modulus of the carbonate rock formation.

9. The method in accordance with claim 8, further comprising the step of:

f) using said dry bulk modulus to determine pore fluid compressibility.

10. The method in accordance with claim 7, further comprising the step of:

d) using the model generated in step (b) to compute intrinsic intergranular and intragranular porosity of the carbonate rock formation.

* * * * *